United States Patent [19]

Crivello et al.

[11] Patent Number: 4,683,317

[45] Date of Patent: Jul. 28, 1987

[54] PHOTOPOLYMERIZABLE ORGANIC COMPOSITIONS AND DIARYLIODONIUM SALTS USED THEREIN

[75] Inventors: James V. Crivello, Clifton Park; Julia L. Lee, Schenectady, both of N.Y.

[73] Assignee: General Electric Company, Schenectady, N.Y.

[21] Appl. No.: 721,244

[22] Filed: Apr. 8, 1985

Related U.S. Application Data

[62] Division of Ser. No. 497,357, May 23, 1983, Pat. No. 4,529,490.

[51] Int. Cl.$^4$ ............................ C07F 9/66; C07F 9/00; C07F 5/02
[52] U.S. Cl. .......................................... 556/64; 568/6; 568/13; 568/16
[58] Field of Search .................. 556/64; 568/6, 13, 16

[56] References Cited

U.S. PATENT DOCUMENTS

| | | | |
|---|---|---|---|
| 4,378,277 | 3/1983 | Smith | 556/64 X |
| 4,394,403 | 7/1983 | Smith | 556/64 X |
| 4,450,360 | 5/1984 | Crivello et al. | 556/64 |
| 4,537,725 | 8/1985 | Irving | 556/64 X |

*Primary Examiner*—Helen M. S. Sneed
*Attorney, Agent, or Firm*—William A. Teoli; James C. Davis, Jr.; James Magee, Jr.

[57] ABSTRACT

Aryliodonium salts resulting from the condensation of aryliodosotosylates and aryl ketones are provided which are used as photoinitiators to effect deep section UV cures. Deep section photopolymerizable organic materials are also provided which can be used as encapsulating agents to encapsulate a wide variety of electronic components.

5 Claims, No Drawings

PHOTOPOLYMERIZABLE ORGANIC COMPOSITIONS AND DIARYLIODONIUM SALTS USED THEREIN

This application is a division of application Ser. No. 497,357, filed May 23, 1983, now U.S. Pat. No. 4,529,490.

BACKGROUND OF THE INVENTION

The present invention relates to aryl ketone containing iodonium salts, their method of synthesis and their use of photoinitiators in photopolymerizable organic materials.

Prior to the present invention, as shown by Smith U.S. Pat. No. 4,378,277, diaryliodonium salts, such as diphenyliodonium hexafluoroarsenate, were used as photoinitiators for effecting the cationic polymerization of epoxy resins. Although the aforementioned diaryliodonium salts were effective in converting epoxy resins to the tack-free state in a relatively short period of time, it was often difficult to achieve a cured epoxy resin product having a satisfactory thickness because the cured film often acted as a barrier to the ultraviolet light required to activate the diaryliodonium salt. Improved thickness of cure was achieved by employing certain arylsulfonium salts, as shown by Smith U.S. Pat. No. 4,173,476. It would be desirable to achieve deeper section cures with UV polymerizable organic materials employing diaryliodonium salts in particular applications.

The present invention is based on our discovery that aryl ketone containing diaryliodonium salts having the formula, $$[RR^1I]^+X^- \quad (1)$$

where R is a $C_{(6-13)}$ monovalent aromatic hydrocarbon radical or halo substituted monovalent aromatic hydrocarbon radical and $R^1$ is a monovalent aryl ketone group which is attached to iodine by a nuclear carbon atom, and $X^-$ is a counter ion, can be used with a wide variety of photopolymerizable organic materials such as epoxy resins, to make deep section photopolymerizable organic materials. The aryl ketone containing diaryliodonium salts of formula (1), can be made by a simple metathesis between a diaryliodonium tosylate precursor and an appropriate counter ion source, such as a hexafluoro metal or metalloid salt. The diaryliodonium tosylate salt precursor can be made by the direct condensation of an aryl iodosotosylate with an aromatic ketone in accordance with the following equation, where Tos$^-$ is tosylate:

$$RI^+ (OH) Tos^- + (R^1)_2C=O \xrightarrow{H^+} [RR^1I]^+ Tos^- + H_2O$$

where R and $R^1$ are as previously defined. A synthesis of diaryliodonium salts involving the direct condensation of aryliodosotosylates has been reported by Koser, Wettach and Smith, Journal of Organic Chemistry, 45, 1944 (1980). As indicated above, conversion of the aryl ketone containing aryliodoniumtosylates to aryl ketone containing diaryliodonium salts of formula (1), can be achieved by a simple metathesis as shown by the following equation:

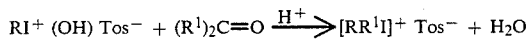

$$[RR^1I]^+Tos^- + MX \rightarrow \text{formula (1)} + M\, Tos^-$$

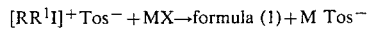

where M is a metal or metalloid.

STATEMENT OF THE INVENTION

There is provided by the present invention, deep section photopolymerizable organic resin compositions comprising
(A) 100 parts of a photopolymerizable organic material and
(B) an effective amount of aryl ketone containing iodonium photoinitiator of formula (1).

Radicals which are included within R of formula (1) are, for example, $C_{(6-13)}$ aromatic hydrocarbon radicals such as phenyl, tolyl, naphthyl, anthryl, and such radicals substituted with up to 1 to 4 monovalent radicals such as $C_{(1-8)}$ alkoxy, $C_{(1-8)}$ alkyl, nitro, chloro, hydroxy, etc,; arylacyl radicals such as benzyl, phenylacyl, etc.; aromatic heterocyclic radicals such as pyridyl, furfuryl, etc.

Radicals which are included within $R^1$ of formula (1) are, for example,

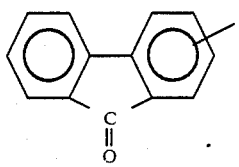

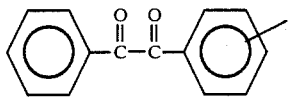

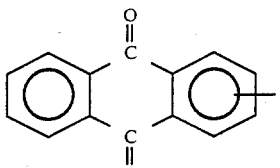

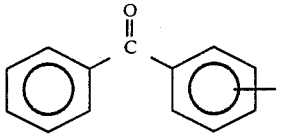

Among the anions which are included by $X^-$ of formula (1) are, for example, $BF_4^-$, $PF_6^-$, $AsF_6^-$, $SbF_6^-$, $ClO_4^-$, $CF_3SO_3^-$, $FSO_3^-$, $CF_3CO_2^-$, $AlCl_4^-$, $BCl_4^-$, $Br^-$, $Cl^-$, $HSO_4^-$, $CH_3CO_2^-$, $NO_3^-$, etc.

Included within the aryl ketone containing iodonium salts of formula (1) are compounds, such as

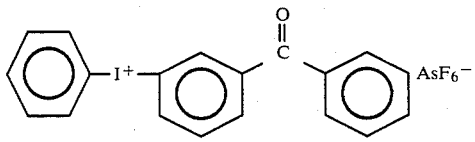

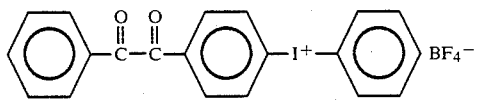

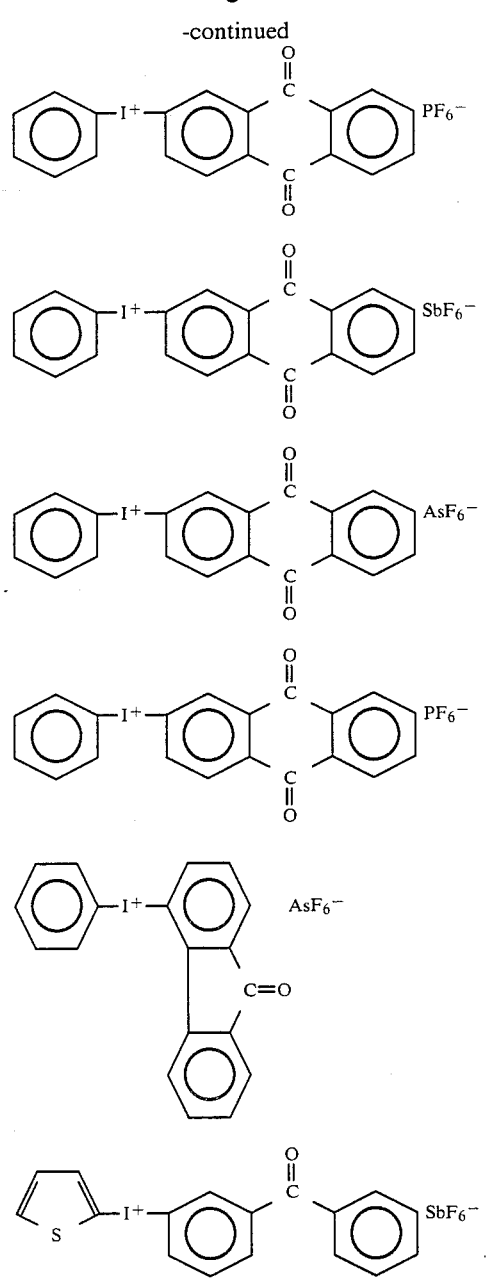

The term "epoxy resin" as utilized in the description of the photopolymerizable compositions of the present invention, includes any monomeric, dimeric or oligomeric or polymeric epoxy material containing one or a plurality of epoxy functional groups. For example, those resins which result from the reaction of bisphenol-A (4,4'-isopropylidenediphenol) and epichlorohydrin, or by the reaction of low molecular weight phenolformaldehyde resin (Novolak resin) with epichlorohydrin, can be used alone or in combination with an epoxy containing compound as a reactive diluent. Such diluents as phenyl glycidyl ether, 4-vinylcyclohexene dioxide, limoene dioxide, 1,2-cyclohexene oxide, glycidyl acrylate, glycidyl methacrylate, styrene oxide, allyl glycidyl ether, etc., may be added as viscosity modifying agents.

In addition, the range of these compounds can be extended to include polymeric materials containing terminal or pendant epoxy groups. Examples of these compounds are vinyl copolymers containing glycidyl acrylate or methacrylate as one of the comonomers. Other classes of epoxy containing polymers amenable to cure using the above cayalysts are epoxysiloxane resins, epoxypolyurethanes and epoxy-polyesters. Such polymers usually have epoxy functional groups at the ends of their chains. Epoxy-siloxane resins and method for making are more particularly shown by E. P. Pluedemann and G. Fanger, J. Am. Chem. Soc, 80 632-5 (1959). As described in the literature, epoxy resins can also be modified in a number of standard ways such as reaction with amines, carboxylic acids, thiols, phenols, alcohols, etc., as shown in U.S. Pat. Nos. 2,935,488; 3,235,620; 3,369,055; 3,379,653, 3,398,211; 3,403,199; 3,563,840; 3,567,797; 3,677,995; etc. Further coreactants which can be used with epoxy resins are hydroxy terminated flexibilizers such as hydroxy terminated polyesters, shown in the Encyclopedia of Polymer Science and Technology, Vol 6, 1967, Interscience Publishers, New York, pp. 209-271 and particularly p. 238.

Included by the photopolymerizable organic materials are thermosetting organic condensation resins of formaldehyde which can be used in the practice of the present invention are, for example, urea type resins, phenol-formaldehyde type resins.

In addition, there can be used melamine thiourea resins, melamine, or urea aldehyde resins, cresol-formaldehyde resins and combinations with other carboxy, hydroxyl, amino and mercapto containing resins, such as polyesters, alkyds and polysulfides.

Some of the vinyl organic prepolymers which can be used to make the polymerizable compositions of the present inventiion are, for example, $CH_2$=CH—O—($CH_2$—$CH_2O)_{n'}$—CH=$CH_2$, where n' is a positive integer having a value up to about 1000 or higher; multifunctional vinylethers, such as 1,2,3,-propane trivinylether, trimethylpropane trivinylether, prepolymers having the formula,

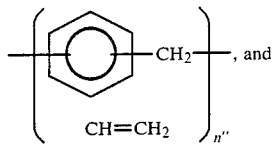

low molecular weight polybutadiene having a voscosity of from 200 to 10,000 centipoises at 25° C., etc. Products resulting from the cure of such compositions can be used as printing inks and other applications typical of thermosetting resins.

A further category of the photopolymerizable organic materials which can be used to make the polymerizable compositions are cyclic ethers which are convertible to thermoplastics. Included by such cyclic ethers are, for example, oxetanes such as 3,3-bis-chloromethyloxethane, alkoxyoxetanes as shown by Schroeter U.S. Pat. No. 3,673,216, assigned to the same assignee as the present invention; oxolanes such as tetrahydrofuran, oxepanes, oxygen containing spiro compounds, thioxane, dioxolane, etc.

In addition to cyclic ethers there are also included cyclic esters such as beta-lactones, for example propiolactone, cyclic amines, such as 1,3,3-trimethylazetidine and organosilicon cyclics, for example, materials included by the formula,

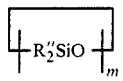

where R'' can be the same or different monovalent organic radical such as methyl or phenyl and m is an integer equal to 3 to 8 inclusive. An example of an organosilicon cyclic is hexamethyltrisiloxane, octamethyltetrasiloxane, etc. The products made in accordance with the present ivention are high molecular weight oils and gums.

In the practice of the present invention the aryl ketone containing iodonium salts of formula (1) can be made by effecting reaction between an aryliodosotosylate and an aromatic ketone at temperatures in the range of from about 25°–125° C. In particular instances, the reaction can be carried out in the melt or a suitable organic solvent can be used to facilitate the reaction. Suitable aromatic ketones which can be used are, for example, benzophenone, acetophenone, propiophenone, 4-benzoylbenzoic acid, 4-benzoylbiphenyl, 4-bromobenzophenone, 2-chlorobenzophenone, 3-nitrobenzophenone, 4,4'-dimethoxybenzophenone, 4-hydroxybenzophenone, 9-fluorenone, thioxanthone, anthriquinone, napthoquinone, acridone, benzil 1-benzoylnapthalene, 1-tetralone, xanthone, 4-chlorothioxanthone, 4-actylbiphenyl, α-bromoacetophenone, etc.

An inert organic solvent can be used in particular situations to facilitate reaction. Such inert organic solvents which may be included are, for example, chloroform, methylene chloride, acetic acid, nitromethane, acetonitrile, carbon tetrachloride, etc.

After the aromatic ketone containing aryliodoniumtosylate can be converted to the aromatic ketone containing aryliodonium salts of formula (1) by a metathesis reaction as previously described employing a metal or metalloid salt, or hydrogen substituted source of a counter ion to provide an appropriate anion included by $X^-$ as previously defined. Suitable metal or metalloid salts which can be used in the metathesis reaction are shown, for example in Crivello U.S. Pat. No. 4,173,551, assigned to the same assignee as the present invention and incorporated herein by reference. Some of these metal or metalloid salts include transition metals such as Sb, Fe, Sn, Bi, Al, Ga, In, T, Zr, Sc, V, Cr, Mn, C, rare earth elements such as the lanthanides, for example, Cd, Pr, Nd, etc., actinides, such as Th, Pa, U, Np, etc, and metalloids such as B, P, As, etc. Recovery of the aryl containing iodonium salts can be achieved by standard techniques empolying such techniques as filtration, use of a centrifuge, etc.

The photopolymerizable composition of the present invention can be made by blending the photopolymerizable organic material with an effective amount of the aryl ketone containing iodonium salt which can be from 0.1% to 15% of the arylketone containing iodonium salt based on the weight of the photopolymerizable organic material. Preferably there can be used from 0.5% to about 5% by weight or aryl ketone containing iodonium salt.

The photocurable compositions of the present invention can containing inactive ingredients such as silica, talc, clay, glass fibers, extenders, hydrated alumina, carbon fibers, process aids, etc., in amounts of up to about 500 parts of filler per 100 parts of the photopolymerizable organic material. The photopolymerizable compositions can be applied to such substrates as metal, rubber, plastic, molded parts of films, paper, wood, glass, cloth, concrete, ceramic, etc.

Some of the applications in which the photocurable compositions of the present invention can be used are, for example, protective, decorative and insulating coatings, pitting compounds, printing inks, sealants, adhesives, molding compounds, wire insulation, textile coatings, laminates, impregnated tape, varnishes, etc.

In order that those skilled in the art will be better able to practice the invention, the following example is given by way of illustration and not by way of limitation. All parts are by weight.

EXAMPLE 1

A mixture of 0.025 mole of phenyliodosotosylate, 0.05 mole of aryl ketone was stirred and heated to 130°–135° C. for 1 hour. During the reaction, the mixture became homogenous and on cooling, it was poured into 100 ml of ethylether. An oil was formed which was washed with diethylether and then dissolved in 50 ml of methyl ethyl ketone. There was added to the resulting solution 5 grams of potassium hexafluoroarsenate. An immediate precipitation of potassium p-toluene sulfonate resulted which was removed by filtration. The solvent was then removed on a rotary evaporator and the resulting solid recrystallized from ethanol. The resulting product was then examined for its UV absorption (λmax) using a Beckman UV spectrophotometer. The following results were obtained:

| Iodonium Salt | Yield | m.p. (°C.) | λ max |
| --- | --- | --- | --- |
| (C₆H₅)–I⁺–C₆H₄–C₆H₄–AsF₆⁻ | 45% | >230 | 293 (ε = 973) |
| C₆H₅–CO–CO–C₆H₄–I⁺–C₆H₅, AsF₆⁻ | 22% | 115–120 | 300 (ε = 549) |

| Iodonium Salt | Yield | m.p. (°C.) | λ max |
|---|---|---|---|
| [structure: dibenzoyl-substituted phenyl-I+-C6H5 AsF6−] | 29% | 143 | 335 (ε = 8,390) |
| [structure: benzoyl phenyl-I+-C6H5 AsF6−] | 26% | 78–85 | 300 (ε = 249) |

EXAMPLE 2

A 1% solution of 3-benzoylphenylphenyliodonium hexafluoroarsenate and limonene dioxide was poured into an aluminum cup and irradiated for 5 minutes at a distance of 5 inches from A GE H3T7 medium pressure mercury arc lamp. It was found that the solution cured to the bottom of the aluminum cup which was a thickness of 70.8 mils.

EXAMPLE 3

The same procedure was repeated, except a 1% solution of diphenyliodonium hexafluoroarsenate in limonene dioxide was used. At the end of the irradiation period, following the same procedure the solution was still incompletely cured at the surface and uncured below the surface. A 1% mixture of 3-benzoylphenyl-phenyliodonium hexafluoroarsenate and Epon 812, Shell Chemical Company, a mixture of bisphenol-A diglycidyl ether and butyldiglycidyl ether was irradiated for 2.5 minutes as described in Example 2.

| Photoinitiator | Film Thickness (mils) |
|---|---|
| (Ph)2I+AsF6− | 34.7 |
| [structure: benzoyl phenyl-I+-C6H5 AsF6−] 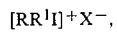 | 58.1 |

The above results show that the UV curable compositions of the present invention can be cured to a greater thickness than the UV curable compositions of the prior art using diphenyliodonium salts as a photoinitiator.

EXAMPLE 4

A 1% solution of photoinitiator in 3,4-epoxycyclohexylmethyl-3',4'-epoxycyclohexane carboxylate, (ERL 4221) of the Union Carbide Chemical Company, was irradiated for 1 minute in an aluminum cup following the procedure of Example 3. The following results were obtained:

| Photoinitiator | Film Thickness (mils) |
|---|---|
| [structure: dibenzoyl-type with I+-C6H5 AsF6−] | 23.8 |

The above procedure was repeated except that in place of the aromatic ketone containing diphenyliodonium salt of the present invention, there was employed a 1% solution of diphenyliodonium hexaflurorarsenate. There was obtained a cured film having a thickness of about 14.3 mils. The above results further show that the UV curable compositions of the present invention exhibit superior deep section curing characteristics as compared to the UV curable compositions of the prior art.

Although the above examples are directed to only a few of the very many variables which can be used in the practice of the present invention, it should be understood that the present invention is directed to a much broader variety of deep section UV curable cationically polymerizable compositions, aryl ketone containing iodonium salts and methods for making such materials as shown in the description preceding these examples.

What we claim as new and desire to secure by Letters Patent of the United States is:

1. Arylketone containing iodonium salts of the formula $$[RR^1I]^+X^-,$$

where R is a $C_{(6-13)}$ monovalent aromatic hydrocarbon radical or halo substituted $C_{(6-13)}$ monovalent aromatic hydrocarbon radical and $R^1$ is a monovalent aryl ketone group which is attached to iodine to form a carbon-iodine linkage selected from the class consisting of

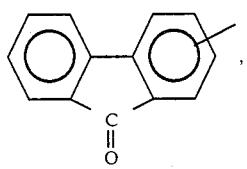

and X⁻ is a counter ion selected from the class consisting of tosylate, tetrafluoroborate, hexafluorophosphate, hexafluoroarsenate, and hexafluoroantimonate.

2. An aryl ketone containing iodonium salt in accordance with claim 1 of the formula,

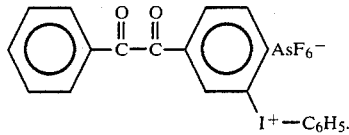

3. An aryl ketone containing iodonium salt in accordance with claim 1 of the formula,

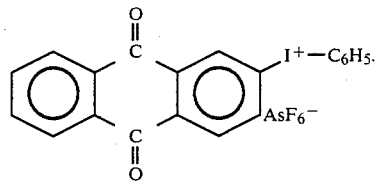

4. An aryl ketone containing iodonium salt in accordance with claim 1 of the formula,

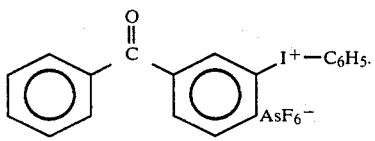

5. An aryl ketone containing iodonium salt in accordance with claim 1 of the formula,

* * * * *

UNITED STATES PATENT AND TRADEMARK OFFICE
CERTIFICATE OF CORRECTION

PATENT NO. : 4,683,317
DATED : July 28, 1987
INVENTOR(S) : James V. Crivello and Julia L. Lee It is certified that error appears in the above-identified patent and that said Letters Patent is hereby corrected as shown below:

Column 9, line 1, before the first line, insert

--  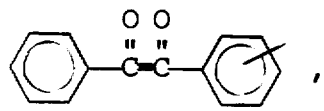,

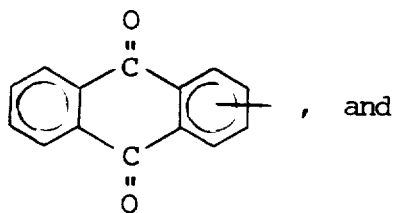 , and

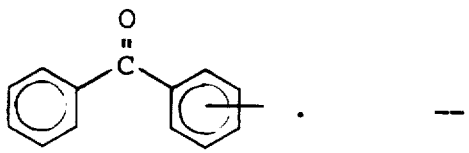 .  --

Signed and Sealed this

Tenth Day of November, 1987

*Attest:*

DONALD J. QUIGG

*Attesting Officer*     *Commissioner of Patents and Trademarks*